United States Patent

Braquet et al.

[11] Patent Number: 5,118,674
[45] Date of Patent: Jun. 2, 1992

[54] 3-(N-METHYL-N-ALKYL)-AMINO 2-METHOXYMETHYLENE PROPAN 1-OL DERIVATIVES, A PREPARATION PROCESS OF THE SAME AND THERAPEUTICAL COMPOSITIONS CONTAINING THEM

[75] Inventors: Pierre Braquet, Garches; Colette Broquet, Boulogne; Bénédicte Vandamme, Versaille; Paola Principe-Nicolas, Paris, all of France

[73] Assignee: Societe de Conseils de Recherches et d'Applications Scientifiques (S.C.R.A.S.), France

[21] Appl. No.: 618,700

[22] Filed: Nov. 27, 1990

[30] Foreign Application Priority Data

Dec. 19, 1989 [GB] United Kingdom ............. 8928580

[51] Int. Cl.$^5$ ............. A61K 31/685; C07F 9/10
[52] U.S. Cl. ............. 514/77; 514/75; 514/76; 514/79; 514/89; 514/91; 514/114; 514/351; 514/427; 514/428; 514/478; 514/513; 546/22; 546/246; 546/329; 546/334; 546/335; 546/347; 548/413; 548/561; 548/566; 548/579; 560/155; 560/157; 560/159; 558/166; 558/169
[58] Field of Search ............. 546/22, 347, 329, 246, 546/334, 335; 560/155, 157, 159; 568/671; 558/169, 166; 514/75, 79, 76, 89, 91, 114, 513, 663, 478, 626, 351, 427, 428; 548/579, 413, 561, 566

[56] References Cited

FOREIGN PATENT DOCUMENTS 2006492  1/1990  Japan ............. 558/169
2020663  11/1979  United Kingdom ............. 558/166

Primary Examiner—Glennon H. Hollrah
Assistant Examiner—Shailendra Kumar
Attorney, Agent, or Firm—Lucas & Just

[57] ABSTRACT

The invention relates to 3-(N-methyl-N-alkyl)-amino 2-methoxymethylene propan 1-ol derivatives of the formula

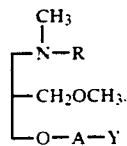

wherein R stands for an alkyl chain, A stands for:

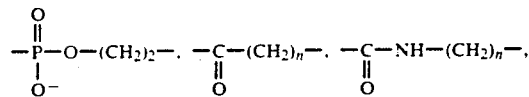

and Y represents various quaternary ammonia, to a preparation process of said compounds and to therapeutic compositions containing the same.

2 Claims, No Drawings

3-(N-METHYL-N-ALKYL)-AMINO 2-METHOXYMETHYLENE PROPAN 1-OL DERIVATIVES, A PREPARATION PROCESS OF THE SAME AND THERAPEUTICAL COMPOSITIONS CONTAINING THEM

The present invention relates to new phospholipid derivatives and, more particularly, to new 3-(N-methyl-N-alkyl)-amino 2-methoxymethylene propan 1-ol derivatives. These new phospholipid compounds are of the following formula:

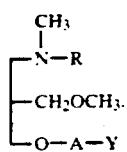
I wherein:
R stands for an alkyl chain of from 10 to 20 carbon atoms;
A stands for:

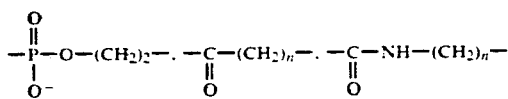

n being an integer of from 2 to 10;
Y represents the following quaternary ammonia: ammonium, alkylammonium, dialkylammonium, trialkylammonium, pyridinium, piperidinium, pyrrolium or pyrrolidinium, each alkyl group having from 1 to 6 carbon atoms,
and therapeutically acceptable salts thereof.

The compounds are more particularly interesting for their anti-tumor activity, which has been found to be far more important than closely related compounds of the state of the art such as, for instance, those described in "Synthesis of Thioether Phosphocholine Analogues" (Eimar BOSIES, Dieter B. J. HERRMANN, Uwe BICKER, Rudi GALL and Wulf PAHIKE - LIPIDS. Vol 22. No. 11, 1987, p. 947-951).

The invention relates, also, to a preparation process of the compounds of the general formula I, said process comprising reacting, in an aprotic solvent, in presence of triethylamine, at a temperature of from 0° to 80° C., under nitrogen circulation, the compound

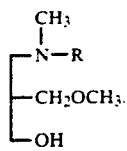
II wherein R is as above defined, on a stoichiometric excess of from 10 to 100% of a compound selected from within

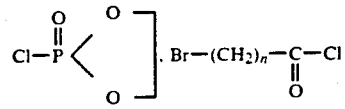

or $O=C=N(CH_2)_nBr$ (n being as above defined), and on a stoichiometric excess of from 30 to 50% of a compound Z, selected from an amine associated with the above defined quaternary ammonia of the formula Y, namely ammoniac, N-alkyl-amine, N,N-dialkylamine, N,N,N-trialkylamine, pyridine, piperidine, pyrrole or pyrrolidine. Of course, in some cases, the reactant Z may be also the solvent of the reaction. So, the definition "a stoichiometric excess" is meaningless.

The process may be illustrated by the following reaction scheme I.

REACTION SCHEME I

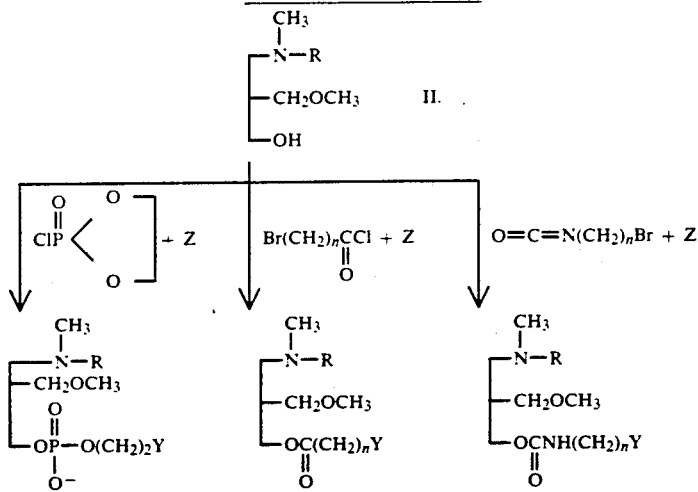

The invention relates, finally, to therapeutical compositions containing one of the compounds I as an active ingredient therein, in association with appropriate diluents and/or carriers.

The starting material II may be prepared as summarized in the following reaction scheme II and described in detail in the following preparative examples 1 to 9 wherein R stands for $C_{12}H_{25}$, $C_{16}H_{33}$ and $C_{18}H_{37}$.

PREPARATIVE EXAMPLES

1. Diethyl 2-phenyl 1,3-dioxane 5,5-dicarboxylate 1

A mixture of diethyl bis-(hydroxymethyl)-malonate (27 gr, 0.12 mole), freshly distilled benzaldehyde (12.5 ml, 0.12 mole) and p-toluene sulfonic acid (0.2 gr) in 250 ml of dry toluene was refluxed for 3 hours using a Dean Stark apparatus. The toluene was eliminated in vacuo and the residue was distilled.

$E_{0.5}$: 170° C. (29.5 gr, yield 78%)
Molecular weight = 308
IR: 1 740 cm$^{-1}$ (C=O)
$^1$HNMR 60 MHz CDCl$_3$, TMS
δ: 7.35 (s, 5H, φ); 5.4 (s, 1H, CHφ); 4.8 (d, 2H); 4.2 (m, 6H, 2H + OC$\underline{H}_2$CH$_3$); 1.2 (m, 6H, OCH$_2$C$\underline{H}_3$)

2. 5-ethoxycarbonyl 2-phenyl 1,3-dioxane 5-carboxylic acid 2

25 gr of 1 (0.08 mol) were added to a solution of 6.6 gr of KOH (0.11 mol) in 140 ml ethanol. After stirring for 4 hours at room temperature, the ethanol was evaporated and the residue was treated with HCl 1N (125 ml) at 0° C. The precipitate was filtered off, washed and dried.

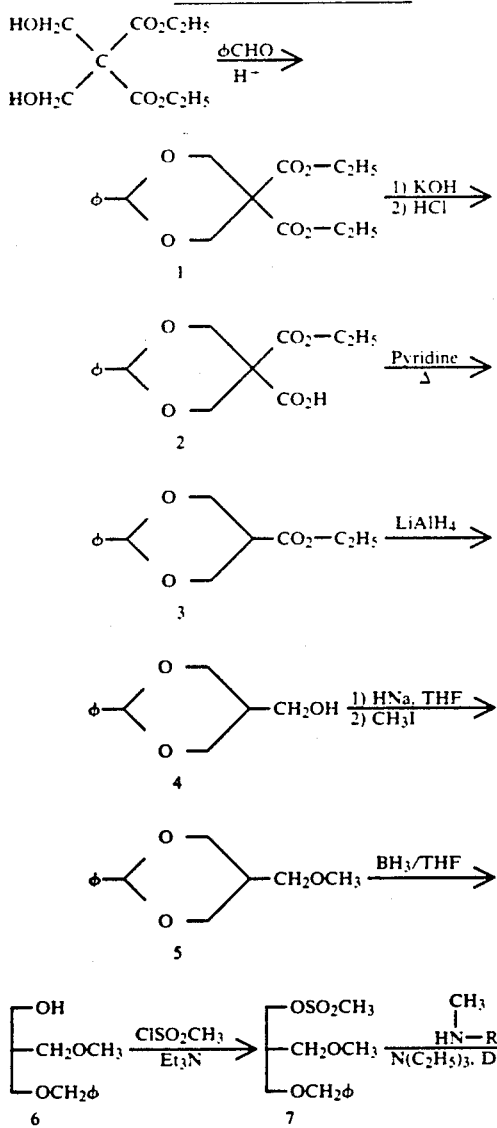

21.6 gr of 2 were obtained (95%). mp 108° C.
Molecular weight = 280
IR (cm$^{-1}$): 3400 (OH); 3100-3040 (φ); 1740 (COOEt); 1690 (COOH); 1100 (C—O—)
$^1$HNMR 60 MHz; CDCl$_3$, TMS.
δ: 7.4 (s, 5H, φ); 5.5 (s, 1H, CHφ); 4.9 (d, 2H, CH$_2$); 4.25 (m, 4H, 2H and OC$\underline{H}_2$CH$_3$); 1.3 (t, 3H, OCH$_2$C$\underline{H}_3$)

3. Ethyl 2-phenyl 1,3-dioxane 5-carboxylate 3

9.2 gr (0.033 mol) of 2 in 20 ml dry-pyridine were refluxed for 5 hours. Pyridine was eliminated in vacuo, the residue was dissolved in CH$_2$Cl$_2$, washed with water, then with brine, dried and evaporated, to give 3 (6.8 gr, 88%) mp 69° C.
Molecular weight = 236
IR: 1 740 cm$^{-1}$ (C=O)
$^1$HNMR. 60 MHz, CDCl$_3$, TMS δ: 7.4 (s, 5H, φ); 5.4 (d, 1H, CHφ); 3.8-4.8 (m, 6H); 3.2 (m, 1H, H—C—CO$_2$Et); 1.3 (m. 3H, OCH$_2$C$\underline{H}_3$).

4. 5-hydroxymethylene 2-phenyl 1,3-dioxane 4

To a mixture of 0.62 gr of LiAlH$_4$ (0.016 mol) in absolute diethyl-ether (80 ml), was added, slowly, a solution of 6.8 g of 3 (0.029 mol) in 60 ml of absolute diethylether. The mixture was stirred for 4 hours at room temperature. Then, at 0° C., ethyl acetate (8 ml), water (4 ml) and NaOH 15% (4 ml) were added. The ethereal layer was decanted, dried and evaporated to afford 5.12 gr (92%) of 4, as a yellow oil. Molecular weight = 194
TLC rf: 0.5 (CH$_2$Cl$_2$) on alumina.
IR: 3430 cm$^{-1}$ (OH)
$^1$HNMR 60 MHz, CDCl$_3$, TMS δ: 7.4 (s, 5H, φ); 5.3 (d, 1H, CHφ); 4.3-3.2 (m, 6H); 2.2 (m, 1H, C$\underline{H}$—CH$_2$OH); 1.3 (1H, OH)

5. 5-methoxymethylene 2-phenyl 1,3-dioxane 5

To a mixture of HNa (50%, 1.06 gr) in 40 ml of dry THF, stirred at 0° C., a solution of 5.12 gr of 4 in 40 ml THF was added dropwise. After 30 min, CH$_3$I (6.6 ml) was added and the mixture was stirred at 0° C. for 6 hours, then overnight at room temperature. Water was added and the mixture was extracted with diethyl-ether, the organic layer was washed with water until neutral, then with brine, dried and evaporated. The residue was purified on alumina column (eluent CH$_2$Cl$_2$) to yield 4.8 gr of 5 (86%).
Molecular weight = 208
TLC rf: 0.86 (CH$_2$Cl$_2$) alumina.
IR (cm$^{-1}$): 3100-3040 (φ), 1100 (C—O—)
HNMR, 60 MHz, CDCl$_3$, TMS
δ: 7.4 (s, 5H, φ); 5.5 (d, 1H, H—C—φ); 4.8-3.2 (m, 9H); 2.3 (m, 1H, C$\underline{H}$—CH$_2$OMe).

6. 2-methoxymethylene 1-0-benzyl propan 1,3-diol 6

To 5 (5.4 gr, 0.026 mol) stirred at 0° C., a solution of BH$_3$ in THF (M, 52 ml) was added dropwise. The mixture was stirred at room temperature for 48 hours, then -continued
REACTION SCHEME II

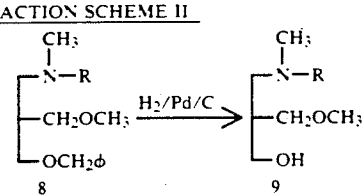

was quenched with cold water at 0° C. and extracted with diethylether. After elimination of the solvent, the crude product was chromatographed on silicagel (eluent CH$_2$Cl$_2$ then CH$_2$Cl$_2$/MeOH 99:1) to give 6 (4 gr, 73%) as a viscous oil.

Molecular weight = 210
TLC rf: 0.24 (CH$_2$Cl$_2$), alumina
IR (cm$^{-1}$) 3450 (OH); 3100-3040 (φ); 1100 (C—O—)
$^1$HNMR 60 MHz, CDCl$_3$, TMS δ: 7.3 (s, 5H, φ); 4.5 (s, 2H, CH$_2$φ); 3.1-3.7 (m, 10 H); 2.1 (m, 1H, CH—CH$_2$O—); 2.6 (1H, OH)

7. 3-0. methylsulfonyl, 2-methoxymethylene 1-0 benzyl propan 1,3-diol 7

To a solution of 6 (4 gr, 0.019 mol), in a mixture of 60 ml of dry diethyl ether and 40 ml of dry CH$_2$Cl$_2$, was added, dropwise, ClSO$_2$Me (2.24 ml; 0.029 mol). The mixture was stirred at room temperature for 24 hours. After extraction with CH$_2$Cl$_2$, the organic layer was washed with brine till pH 7 and dried. The solvent was evaporated and the residue was chromatographed on silicagel (eluent CH$_2$Cl$_2$/MeOH 99:1) to give 7 (4.6 g, 84%) as viscous oil.

Molecular weight = 288
TLC rf: 0.7 (CH$_2$Cl$_2$/MeOH: 95:5) silicagel
IR (cm$^{-1}$): 1350 (SO$_2$); 1170 (SO$_2$); 1100 (C—O—C)
$^1$HRMN 60 MHz, CDCl$_3$, TMS (δ) 4.35 (d, 2H, CH$_2$OSO$_2$); 3.3-3.6 (m, 7H); 3.0 (s, 3H, SO$_2$CH$_3$); 2.3 (m, 1H, CH—CH$_2$O).

The different N,N-(methyl alkyl) amines, except N,N-(octadecyl methyl)amine (Aldrich) were obtained from the corresponding alkyl halide and methyl amine according to I. G. Farbening A. G. Fr. 784,599, Jul. 22, 1935.

8. 1-N,N-(methyl alkyl)amino 2-methoxymethylene 3-0-benzyloxy propane 8

7 (0.016 mol) dissolved in DMSO (15 ml) was added to a solution of N,N-(methyl alkyl)amine (0.016 mol) and Et$_3$N (1.4 ml) in DMSO (60 ml). The mixture was stirred at 80° C. for 24 hours. After elimination of DMSO under reduced pressure, the residue was dissolved in CH$_2$Cl$_2$, the organic phase was washed with water and dried. The crude product was chromatographed (eluent CH$_2$Cl$_2$/MeOH 98:2) to give 8.

8a R = C$_{12}$H$_{25}$ (yield 50%—viscous oil) TLC rf: 0.16 (CH$_2$Cl$_2$/MeOH 95:5)
8b R = C$_{16}$H$_{33}$ (yield 61%—viscous oil) TLC rf: 0.18 (CH$_2$Cl$_2$/MeOH 95:5)
8c R = C$_{18}$H$_{37}$ (yield 58%—viscous oil) TLC rf: 0.18 (CH$_2$Cl$_2$/MeOH 95:5)
IR: 1100 (C—O—) cm$^{-1}$
$^1$HNMR 60 MHz, CDCl$_3$, TMS δ: 7.3 (s, 5H, φ); 4.5 (s, 2H, CH$_2$φ); 3.3-3.6 (m, 7H, OCH$_3$, 2CH$_2$O); 2.15-2.4 (m, 7H,

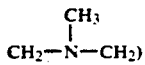

1.8 (m, 1H, CH—CH$_2$O); 1.25 large sing, 2nH, NCH$_2$(CH$_2$)$_n$ CH$_3$; 0.9 (t, 3H, CH$_3$)

9. 3-N,N-(methyl alkyl)amino 2-methoxymethylene propan 1-ol 9

Obtained by hydrogenolysis of 8 in CHCl$_3$ with Pd/C 10% (40 psi, 5 hours at 40° C.).

9a R = C$_{12}$H$_{25}$ (yield 79%) TLC rf: 0.36 (CH$_2$Cl$_2$/MeOH 90:10)
9b R = C$_{16}$H$_{33}$ (yield 87%) TLC rf: 0.39 (CH$_2$Cl$_2$/MeOH 90:10)
9c R = C$_{18}$H$_{37}$ (yield 85%) TLC rf: 0.39 (CH$_2$Cl$_2$/MeOH 90:10) Molecular weight = 385
IR (cm$^{-1}$): 3450 (OH) ; 1100 (C—O—C)
$^1$HNMR, 60 MHz, CDCl$_3$, TMS δ: 5.3 (1H, OH); 3.3-3.8 (m, 7H, OCH$_3$, 2 CH$_2$O) 2.7 (m, 7H, NCH$_3$ and CH$_2$—N—CH$_2$); 2.2 (m, 1H, CH—CH$_2$O); 1.25 large sing, 2nH, NCH$_2$(CH$_2$)$_n$CH$_3$; 0.9 (t, 3H, CH$_3$)

The invention will be better understood from the description of the following examples.

EXAMPLE 10

3-N,N-(methyl alkyl)amino 2-methoxymethylene propan 1-0 phosphocholine

Alkyl stands for —C$_{12}$H$_{25}$, —C$_{16}$H$_{33}$ and —C$_{18}$H$_{37}$

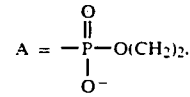

$Y = —N^+(CH_3)_3$

To a cooled (5° C.), stirred solution of 9 (7 mmol) and 3 ml of NEt$_3$ in dry benzene (20 ml), was added 2-chloro 2-oxo 1,3,2-dioxaphospholane (2 gr, 14 mmol) in 4 ml of C$_6$H$_6$, under nitrogen circulation. The mixture was stirred at room temperature for 8 hours, then filtered. The filtrate was evaporated off under reduced pressure. The residue was dissolved in dry CH$_3$CN (50 ml) and transferred in a reactor. 30 ml of CH$_3$CN saturated by gaseous NMe$_3$ were added and the mixture was heated at 65° C. for 24 hours. The solvent was evaporated and the residue was chromatographed on silicagel (eluent CHCl$_3$/MeOH 90:10; 70:30; 30:70 then MeOH) to yield the title compound.

10a R = C$_{12}$H$_{25}$ (yield 40%) MH$^+$ = 467 TLC rf: 0.25 (CHCl$_3$/MeOH/NH$_4$OH 70:30:7)
10b R = C$_{16}$H$_{33}$ (yield 44%) MH$^+$ = 523 TLC rf: 0.26 (CHCl$_3$/MeOH/NH$_4$OH 70:30:7)
10c R = C$_{18}$H$_{37}$ (yield 45%) MH$^+$ = 551 TLC rf: 0.26 (CHCl$_3$/MeOH/NH$_4$OH 70:30:7)
IR (cm$^{-1}$): 1240 (P=O); 1100 (C—O—C); 1040 (P—O)
$^1$HNMR, 500 MHz, CH$_3$OD, TMS δ: 0.85 (t, 3H, CH$_3$); 1.2 [large sing, 2nH, (CH$_2$)$_n$]; 1.45 (m, 2H, NCH$_2$CH$_2$); 2.0 (m, 1H, CH—CH$_2$O); 2.15 (s, 3H, NCH$_3$); 2.3 (m, 4H, CH$_2$—N—CH$_2$); 3.15 [s, 9H, N(CH$_3$)$_3$]; 3.35 (s, 3H, OCH$_3$); 3.4 (d, 2H, CH$_2$—OCH$_3$); 3.55 (m, 2H, CH$_2$N$^+$); 3.85 (m, 2H, CH$_2$OP); 4.25 (m, 2H, POCH$_2$).

EXAMPLE 11

3-N,N-(methyl alkyl)amino 2-methoxymethylene 1-[6′-(N-pyridinium)pentylcarboxy] propane bromide Alkyl stands for —C$_{12}$H$_{25}$, —C$_{16}$H$_{33}$ and —C$_{18}$H$_{37}$

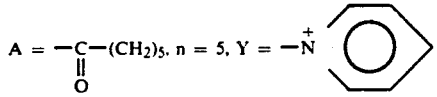

A solution of 9 (9 mmol) and triethylamine (25 mmol) in 15 ml of ethanol-free trichloromethane, were added dropwise to a solution of 10 mmol of 5-bromohexanoyl chloride in 10 ml of the same solvent at 0° C. under nitrogen circulation. The mixture was then stirred for about 15 hours at room temperature. After evaporation of solvent, 30 ml of dry pyridine was added to the obtained residue, and the mixture was then stirred at 80° C. under nitrogen circulation for 24 hours. Pyridine was eliminated in vacuo and the residue was purified by column chromatography (eluent CHCl$_3$, then CHCl$_3$/MeOH 90:10) to yield the title compound.

11a R = C$_{12}$H$_{25}$ (yield 68%)
11b R = C$_{16}$H$_{33}$ (yield 60%)
11c R = C$_{18}$H$_{37}$ (yield 71%)

IR (cm$^{-1}$): 1100 (C—O—C); 1740 (C=O); 1640 (pyridine)

$^1$HNMR, 500 MHz, CDCl$_3$, TMS δ: 0.85 (t, 3H, CH$_3$); 1.2 [large sing, 2nH, (CH$_2$)n]; 2.2 (s, 3H, NCH$_3$); 2.35 [t, 2H, C(O)CH$_2$]; 3.35 (s, 3H, OCH$_3$); 3.45 (d, 2H, CH$_2$—OCH$_3$)

EXAMPLE 12

3-N,N-(methyl alkyl)amino 2-methoxymethylene 1-[6'-(N-pyridinium) pentylcarbamoyloxy] propane bromide Alkyl stands for —C$_{12}$H$_{25}$, —C$_{16}$H$_{33}$ and —C$_{18}$H$_{37}$

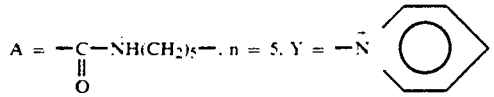

A mixture of 9 (9 mmol), 5-bromopentylisocyanate (12 mmol) in benzene and 30 ml of pyridine, was heated for two days at 80° C. under nitrogen circulation. Pyridine was eliminated in vacuo and the obtained residue was dissolved in CHCl$_3$, washed and dried. The solvent was evaporated and the residue was chromatographed (CHCl$_3$ then CHCl$_3$/MeOH, 95:5, 90:10) to give the title compound.

12a R = C$_{12}$H$_{25}$ (yield 49%)
12b R = C$_{16}$H$_{23}$ (yield 52%)
12c R = C$_{18}$H$_{37}$ (yield 62%)

IR (cm$^{-1}$): 1100 (C—O—C); 1640 (pyridine) 1720 (CONH); 3350 (NH)

$^1$HNMR, 500 MHz, CDCl$_3$, TMS δ: 0.90 (t, 3H, CH$_3$); 1.2 [large sing, 2nH, (CH$_2$)$_n$]; 2.15 (s, 3H, NCH$_3$); 3.25 [t, 2H, C(O)NHCH$_2$]; 3.35 (s, 3H, OCH$_3$); 3.4 (d, 2H, CH$_2$—OCH$_3$); 5.1 (t, 2H, CH$_2$N$^+$); 5.6 (d, 1H, NH)

EXAMPLE 13

3-N,N-(methyl alkyl)amino 2-methoxymethylene 1-[6'-(N-piperidinium)pentylcarbamoyloxy]propane bromide Alkyl stands for —C$_{12}$H$_{35}$, —C$_{16}$H$_{33}$ and —C$_{18}$H$_{37}$

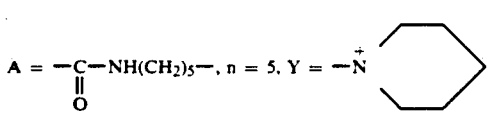

This compound is prepared by the same process as described in example 12, but using piperidine instead of pyridine.

13a R = C$_{12}$H$_{25}$ (yield 49%)
13b R = C$_{16}$H$_{33}$ (yield 42%)
13c R = C$_{18}$H$_{37}$ (yield 53%)

IR (cm$^{-1}$): 1100 (C—O—C); 1720 (CONH); 3350 (NH)

$^1$HNMR, 500 MHz, CDCl$_3$, TMS δ: 0.85 (t, 3H, CH$_3$); 1.2 [large sing, 2nH, (CH$_2$)n]; 2.15 (s, 3H, NCH$_3$); 3.25 [t, 2H, C(O)NHCH$_2$]; 3.35 (s, 3H, OCH$_3$); 3.4 (d, 2H, CH$_2$—O—CH$_3$); 5 (t, 2H, CH$_2$N$^-$); 5.6 (d, 1H, NH)

EXAMPLE 14

3-N,N-(methyl alkyl)amino 2-methoxymethylene 1-[6'-(N-pyrrolium) pentylcarbamoyloxy]propane bromide Alkyl stands for —C$_{12}$H$_{35}$, —C$_{16}$H$_{33}$ and —C$_{18}$H$_{37}$

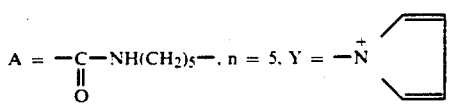

This compound is prepared by the same process as described in example 12, but using pyrrole instead of pyridine.

14a R = C$_{12}$H$_{25}$ (yield 53%)
14b R = C$_{16}$H$_{33}$ (yield 61%)
14c R = C$_{18}$H$_{37}$ (yield 48%)

IR(cm$^{-1}$) 1100 C—O—C); 1720 (CONH); 3350 (NH)

$^1$HNMR, 500 MHz, CDCl$_3$, TMS δ: 0.85 (t, 3H, CH$_3$); 1.2 [large sing, 2nH, (CH$_2$)n]; 2.2 (s, 3H, NCH$_3$); 3.25 [t, 2H, C(O)NHCH$_2$]; 3.35 (s, 3H, OCH$_3$); 3.4 (d, 2H, CH$_2$—O—CH$_3$); 5 (t, 2H, CH$_2$N$^+$); 5.6 (d, 1H, NH)

EXAMPLE 15

3-N,N-(methyl alkyl)amino 2-methoxymethylene 1-[6'-(N-pyrrolidinium)pentylcarbamoyloxy]propane bromide Alkyl stands for —C$_{16}$H$_{33}$, —C$_{17}$H$_{35}$ and —C$_{18}$H$_{37}$

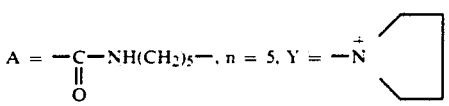

This compound is prepared by the same procedure as described in example 12, but using pyrrolidine instead of pyridine.

15a R = C$_{12}$H$_{25}$ (yield 49%)
15b R = C$_{16}$H$_{33}$ (yield 45%)
15c R = C$_{18}$H$_{37}$ (yield 56%)

IR(cm$^{-1}$): 1100 (C—O—C); 1720 (CONH); 3350 (NH)

$^1$HNMR, 500 MHz, CDCl$_3$, TMS δ: 0.85 (t, 3H, CH$_3$); 1.2 [large sing, 2nH, (CH$_2$)n]; 2.15 (s, 3H, NCH$_3$); 3.25 [t, 2H, C(O)NHCH$_2$; 3.35 (s, 3H, OCH$_3$); 3.4 (d, 2H, CH$_2$—O—CH$_3$); 5 (t, 2H, CH$_2$N$^+$); 5.6 (d, 1H, NH)

Toxicity

The toxicity of the compounds of the invention, has been determined per os on mice, by usual methods. Their LD$_{50}$ values are higher than 650 mg/kg.

Pharmacology

The compounds of the invention have been examined for their ability to inhibit in vitro tumor cell proliferation.

They inhibit HL60 and A.427 tumor cell proliferation after 24 hours.

HL60: promyelocytic leukemia cell line

A.427: lung carcinoma cell line

They show a cytostatic effect at the dose of 0.02 mM which is not a toxic dose for the two human tumor cell lines. Overall, the lung carcinoma cell line resulted more sensitive than the promyelocytic leukemia cell line.

The effect of the compounds of the invention on long-term proliferation has been more precisely described above.

All of the examples of the invention have been tested and compared with one of the first related compounds discovered as inhibiting the neoplastic cell-growth: the 1-0-octadecyl-2-0-methylglycero- 3-phosphocholine (ET180CH$_3$ or methoxy PAF; Andreesen, 1988).

For this study, a lung carcinoma cell line, called A.427, have been used: they are anchorage-dependent cells.

The A.427 cells were grown in EMEM medium containing sodium pyruvate and non-essential amino acids (Flow Labs), supplemented with 10% foetal bovine serum (FBS; Gibco). The growth media contained 100 U/ml of penicillin and 100 μg/ml of streptomycin (Flow Labs).

The compounds of the invention and the reference compound ET180CH$_3$ (Bachem; Switzerland) were dissolved in a solution containing 60% ethanol and 40% phosphate buffer saline (PBS; Flow Labs). Serial dilutions were prepared in PBS. The dose tested was 0.02 mM. The treatment time lasted 24 hours at 37° C.

The effect of the compounds of the invention on long-term cell proliferation and survival has been evaluated by studying the plating efficiency and colony morphology of A.427. To carry out this study, $1.10^3$ A.427 cells, previously treated with the compounds of the invention for 24 hours, were seeded into 25 cm$^2$ growth area tissue culture flasks.

These cell cultures were then incubated at 37° C. for 15 days. At the end of this incubation time, the cell cultures were rinsed twice with PBS, fixed with 70% ethanol for 30 minutes and stained for the same length of time with 10% Giemsa (Sigma Chemicals).

The results are expressed as 'relative plating efficiency (P.E.)' values calculated as follows:

$$P.E. = \frac{\text{Number of colonies formed}}{\text{Number of cells plated}} \times 100$$

and summarized in the following table.

It has been found that the colonies formed after treatment of compounds of the invention have lost their regular profile, have a lower reactivity to the Giemsa stain and, overall, have a size which is smaller than that of the untreated colonies.

| COMPOUNDS | P.E. (%) |
|---|---|
| Control | 100 ± 2.2 |
| ET18OCH3 | 33.4 ± 1.5 |
| EX 10-a | 27.1 ± 2.6** |
| EX 10-b | 21.4 ± 1.8* |
| EX 10-c | 14.2 ± 0.9*** |
| EX 11-a | 23.2 ± 2.4* |
| EX 11-b | 18.5 ± 2.1* |
| EX 12-a | 25.6 ± 3.1** |
| EX 12-b | 20.2 ± 2.3** |
| EX 13-b | 19.1 ± 3.6*** |
| EX 13-c | 17.6 ± 2.7* |
| EX 14-a | 22.7 ± 3.1* |
| EX 14-b | 27.3 ± 3.3* |
| EX 14-c | 18.6 ± 2.7** |
| EX 15-b | 21.7 ± 3.3** |
| EX 15-c | 26.4 ± 2.6** |

The statistical symbols refer to the comparison between each example with the reference ET18OCH$_3$. The different symbols: NS, *,  and * mean that the result is respectively not significative, significative, very significative and highly significative.

Posology

In human therapy, the compounds of the invention are preferably administrated by I.V. route. Usual posology is from 2.5 to 5 mg/dm$^2$ per diem, three to six days per months in slow perfusion.

We claim:

1. 3-(N-methyl-N-alkyl)-amino 2-methoxymethylene propan 1-ol derivatives of the general formula:

$$\begin{array}{c} CH_3 \\ | \\ -N-R \\ -CH_2OCH_3 \\ -O-A-Y \end{array} \quad I$$

wherein:
R stands for an alkyl chain of from 10 to 20 carbon atoms;
A stands for:

$$-\overset{O^-}{\underset{\|}{P}}-O-(CH_2)_2-, \quad -\overset{\|}{\underset{O}{C}}-(CH_2)_n-, \quad -\overset{\|}{\underset{O}{C}}-NH-(CH_2)_n-,$$

n being an integer of from 2 to 10;
Y represents the following quaternary ammonia: ammonium, alkylammonium, dialkylammonium, trialkylammonium, pyridinium, piperidinium, pyrrolium or pyrrolidinium, each alkyl group having from 1 to 6 carbon atoms,
and therapeutically acceptable salts thereof.

2. Therapeutic compositions containing an effective amount of at least one compound according claim 1, as an active ingredient, associated with appropriate diluents and/or carriers for the selected administration route.

* * * * *